(12) United States Patent
Ketterl et al.

(10) Patent No.: US 6,678,564 B2
(45) Date of Patent: Jan. 13, 2004

(54) BIO-IMPLANT AND METHOD OF MAKING THE SAME

(75) Inventors: Joseph R. Ketterl, Kent, WA (US); John P. Yarno, Snohomish, WA (US); Scott S. Corbett, III, Portland, OR (US); Thomas R. Clary, Issaquah, WA (US)

(73) Assignees: Advanced Cochlear Systems, Inc., Snoqualmie, WA (US); MicroConnex Corporation, Snoqualmie, WA (US)

( * ) Notice: Subject to any disclaimer, the term of this patent is extended or adjusted under 35 U.S.C. 154(b) by 45 days.

(21) Appl. No.: 10/012,230

(22) Filed: Dec. 6, 2001

(65) Prior Publication Data

US 2003/0109913 A1 Jun. 12, 2003

(51) Int. Cl.$^7$ ............................. A61N 1/05; H05K 3/00
(52) U.S. Cl. ........................................ 607/137; 29/829
(58) Field of Search ................. 607/116–119, 122–128, 607/136–137, 55–57; 600/373–381; 29/825, 829, 846, 849, 850

(56) References Cited

U.S. PATENT DOCUMENTS

| | | | | |
|---|---|---|---|---|
| 4,261,372 A | * | 4/1981 | Hansen et al. | 607/137 |
| 4,284,085 A | * | 8/1981 | Hansen et al. | 607/137 |
| 5,309,910 A | * | 5/1994 | Edwards et al. | 600/381 |
| 6,374,143 B1 | * | 4/2002 | Berrang et al. | 607/137 |

* cited by examiner

Primary Examiner—Jeffrey R. Jastrzab
(74) Attorney, Agent, or Firm—Law Office of Timothy E. Siegel; Timothy E. Siegel

(57) ABSTRACT

A bio-implant having a length and a proximal and a distal end. The bio-implant has at least two lamina of dielectric material joined together, thereby defining a boundary and also defining a side surface that is intersected by this boundary. In addition, at least one set of conductors is interposed between the two lamina and extend lengthwise from the proximal end toward the distal end, each one of the set of conductors being terminated adjacent to the side surface to form a set of conductor terminations. Further, a set of electrode contact points are constructed on the side surface, with each electrode contact point contacting one of said conductor terminations.

8 Claims, 3 Drawing Sheets

BIO-IMPLANT AND METHOD OF MAKING THE SAME

STATEMENT OF GOVERNMENT SUPPORT

The present invention was reduced to practice, in part, with government support under SBIR grant No. 2R44DC0461402A1 awarded by the Small Business Research Program of the Department of Health and Human Services. The United States Government has certain rights in the invention.

BACKGROUND OF THE INVENTION

Today, there are many prospective applications for a high-density multi-electrode biocompatible implant. One of the most important is for a cochlear implant. The cochlea is a snail shaped organ of the inner ear that translates sound waves into bioelectrical nerve impulses. A cochlear implant, by directly electrically stimulating the cochlea can effect hearing restoration in persons otherwise completely deaf and for whom other methods of hearing restoration would be ineffective. Compared to the cochlea, however, which includes approximately 30,000 receptive nerve endings, currently available cochlear implants are crude devices, capable of stimulating the cochlea with a degree of selectivity far beneath what the cochlea is capable of accommodating. Accordingly, in order to effect a more complete hearing restoration, cochlear implants having a higher density of precisely positioned electrode contact points are needed.

Because the cochlea has so many more sensing sites than an implant could possibly have electrode contact points, it is desirable to stimulate the cochlea at points between electrode contact points. This can be effected by "field shaping," in which neighboring electrode contact points are separately controlled to form an electric field that has its maximum at a desired cochlear stimulation point. Unfortunately, in order to perform field shaping it is generally desirable to have electrode contact points that are spaced apart by no more than a few hundred um. Achieving this fine spacing of electrode contact points has proven a challenge to researchers.

The cochlea is not the only site within the body where a high-density implant could be of use, however. The brain, the retina and the heart are just a few other sites within the body where such an implant could be used. Some implants may have to operate for many years without failure. Unfortunately, providing such an implant proves to be quite difficult in practice.

Among the challenges encountered in the construction of an implant having a large number (>30) of closely spaced (<100 um) and precisely positioned electrode contact points is the problem of decomposition in the body due to attack by the body's interstitial fluid (ISF). Any seam in an implant will be attacked by ISF and may eventually come apart. Because of this, it is extremely important that biocompatible materials be used throughout an implant. Moreover, the more that an implant can take the form of a seamless, unitary whole the longer an implant can be expected to last within the body. This requirement conflicts with the greater level of complexity desired of implants.

Researchers at the University of Michigan have designed one type of probe that is currently under test. This probe is made by micro machining a silicon substrate using photolithographic techniques in order to achieve accurate positioning of closely spaced electrode contact points. Unfortunately the materials used are stiff and brittle. Accordingly this probe is not well suited for an application that requires flexibility, such as a cochlear implant.

Additionally, multilayer printed circuit board (PCB) technology has advanced so that multilayer structures having traces on the order of microns thick are now available. There are a number of reasons, however, why this technology has, in general, not been applied to the biomedical arena. First, many of the materials used in PCB manufacture are not biocompatible, or degrade after implantation. Second, even flex circuits made from polyimide, a flexible dielectric, typically do not have the degree of flexibility necessary to facilitate the construction and placement of a cochlear implant.

Accordingly, there is a long-standing, unresolved need for a biocompatible, long-term implant that can precisely stimulate a sensory bodily organ, such as the cochlea.

SUMMARY

In a first separate aspect, the present invention comprises a bio-implant having a length and a proximal and a distal end. The bio-implant has at least two lamina of dielectric material joined together, thereby defining a boundary and also defining a side surface that is intersected by this boundary. In addition, at least one set of conductors is interposed between the two laminae and extend lengthwise from the proximal end toward the distal end, each one of the set of conductors being terminated adjacent to the side surface to form a set of conductor terminations. Further a set of electrode contact points are constructed on the side surface, with each electrode contact point contacting one of said conductor terminations.

In a second separate aspect, the present invention is a method of constructing a bio-implant having a length and a proximal and a distal end. The method requires a first and second laminae of dielectric material, each of these laminae defining a top surface, a lamina side surface, and a proximal end and a distal end. Also required are at least one set of conductors positioned on the top surface of the first lamina, the conductors extending lengthwise from the proximal end toward the distal end, each one of the set of conductors being terminated adjacent to the side surface to form a set of conductor terminations. The second lamina is joined to the first lamina about the set of conductors, thereby defining a boundary and also defining a joined side surface that is intersected by the boundary. Next, a set of electrode contact points is constructed on the joined side surface, each electrode contact point contacting one of the conductor terminations.

The foregoing and other objectives, features and advantages of the invention will be more readily understood upon consideration of the following detailed description of the invention, taken in conjunction with the accompanying drawings.

DETAILED DESCRIPTION OF THE PREFERRED EMBODIMENTS

Figures 1, 2:
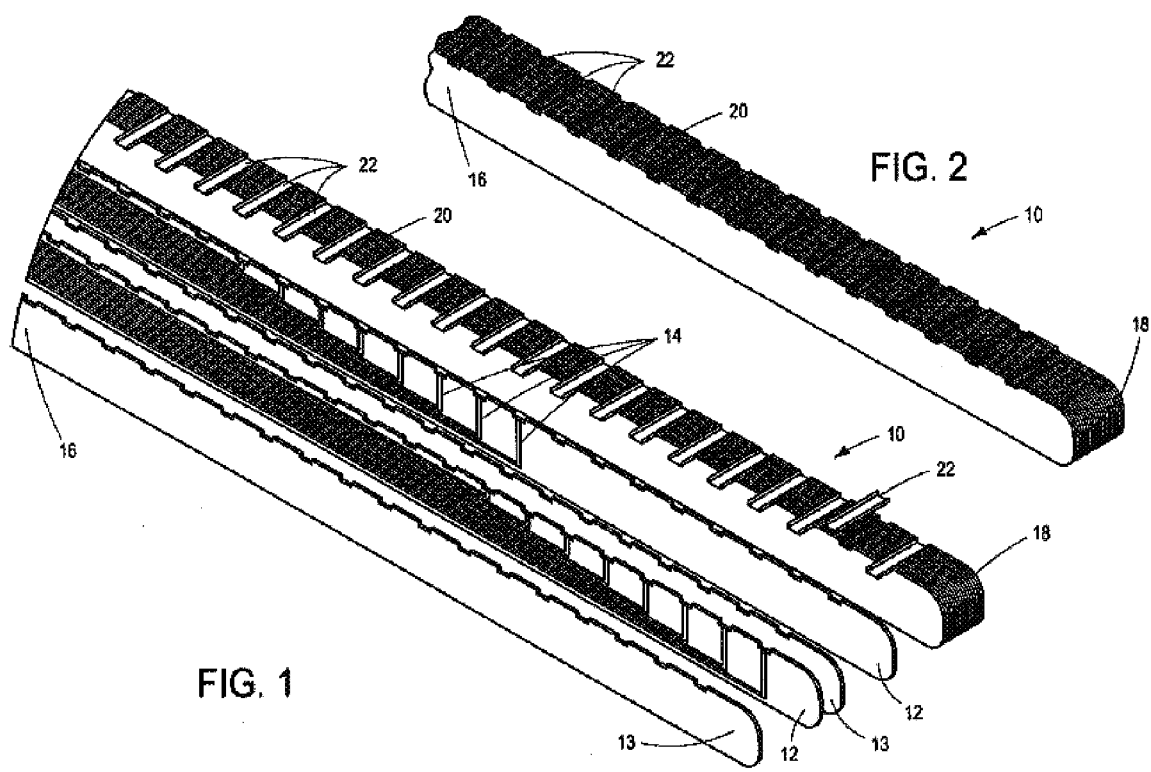
FIG. 1 is an exploded perspective view of a bio-implant according to the present invention.
FIG. 2 is a perspective view of the bio-implant of FIG. 1.
Figure 3:
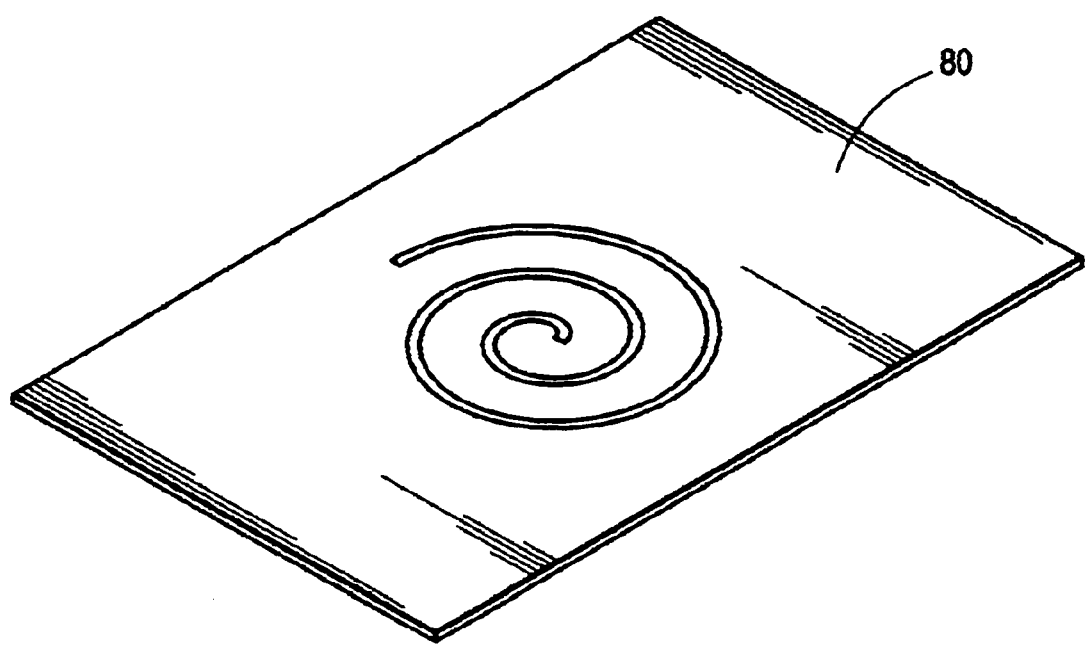
FIG. 3 is a perspective view of a workpiece used for the production of a helical bio-implant according to the present invention.
Figure 4:
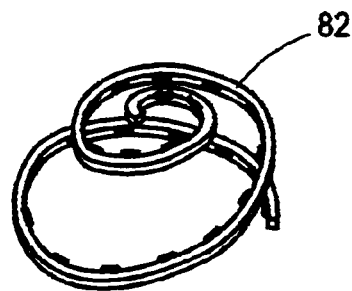
FIG. 4 is a perspective view of a helical bio-implant produced using the workpiece of FIG. 3.
Figure 5:
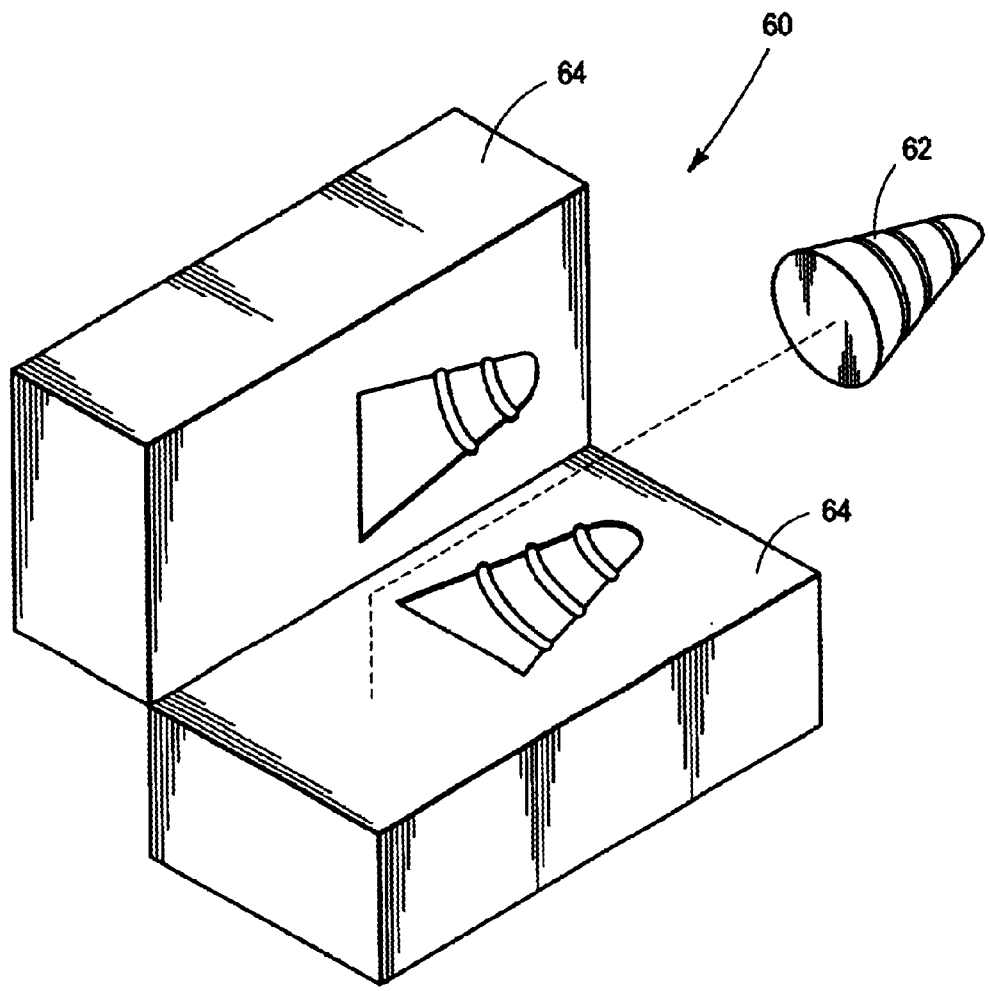
FIG. 5 is a perspective view of a mold adapted to produce a helical bio-implant according to the present invention.
Figure 6:
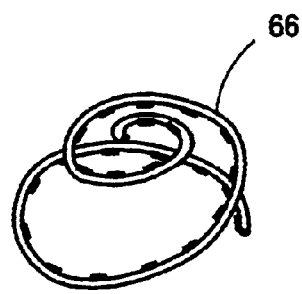
FIG. 6 is a perspective view of a helical bio-implant formed in the mold of FIG. 5.

Referring to FIGS. 1–3 an electrode contact point bearing implant 10 having a proximal end 16 and a distal end 18 includes a set of first laminae 12 made of a dielectric material, for example, liquid crystal polymer (LCP). Conductive traces 14 that extend longitudinally from proximal end 16 toward distal end 18 are constructed on each first laminae 12.

A set of second laminae 13 is interspersed with the set of first laminae 12, electrically isolating one set of traces 14 from another. Second laminae 13 are made of LCP having a lower melting point than the LCP of first laminae 12. As a result, the implant 10 can be heated after being assembled to melt second lamina 13, thereby causing the entire structure to fuse together without surrendering the structural stability provided by first laminae 12.

Each of the conductive traces 14, after it has extended its full longitudinal extent, turns toward an electrode contact point bearing side 20 of the implant 10 and extends to a position either proximal to or abutting side 20. An electrode contact point 22 in the form of a width-wise portion of a plated via is connected to each trace at side 20.

Skilled persons will readily perceive traces 14 could be routed so that the implant 10 could taper inwardly toward the electrode contact point bearing side 20 as it extends from its proximal end 16 to its distal end 18. Alternatively the electrode contact point bearing side 20 could taper inwardly toward the distal end 18. In addition as not all laminae bear traces 14 all the way to the distal end 18, implant 10 could taper inwardly from top to bottom or from bottom to top as it extends distally. Tapering embodiments are of particular importance with respect to cochlear implants, because the cochlea, the prospective location of such an implant, tapers inwardly as it curls towards its center.

In one preferred method of making implant 10, a further margin (not shown) is originally included in the workpiece from which implant 10 is made. Vias are drilled through this margin, so as to contact the termini of the traces 18. The vias are plated with conductive material and then the margin is removed either by mechanical or other means, using for example, an ND:YAG laser. The plated vias are thus bisected to form electrode contact points 22. It should be noted that the vias that are drilled need not be round. If it was found that a square sided via or an elliptical via resulted in electrode contact points 22 having superior electromagnetic properties, these could be formed.

In another preferred method of making implant 10, side 18 is turned to face a laser, which machines a set of indents that are then plated with conductive material to form electrode contact points 22. Persons skilled in the art can recognize that the areas between electrode contact points can be masked during the plating operation, or can be plated and then stripped of plating, for example, by laser ablation or chemical etching. With this method, the electrode contact points could be formed to have differing depths over their top-to-bottom extent.

The electrode contact points may be created by any of a number of well known techniques including sputter deposition, electroless or electrolytic (electroplating) deposition. An inert base metalization can be applied by one of the above means, followed by deposition of a selective metal suitable for neural excitation, including iridium or iridium oxide. Iridium oxide can be deposited on the base metal for example by sputter deposition, by electroplating or by activation. Iridium may be built up through cyclic voltametry. Surfaces may be plasma etched prior to sputtering, to increase adhesion.

In a preferred embodiment, laminae 12 and 13 are 12 $\mu$m (0.5 mils) thick. In a preferred embodiment 8 first laminae are included in implant 10. Conductive traces 14 are 125 $\mu$m (5 mils) wide and 5 $\mu$m (0.2 mils) thick. Eight traces 14 are accommodated per laminae 12, for a total of 64 traces and 64 electrode contact points. Electrode contact points 22 are made by forming vias having a diameter of 30 $\mu$m (1.2 mils) thick, electroplating these vias and bisecting them using a laser. The electrode contact points are spaced 200 $\mu$m (8 mils) apart. In one preferred embodiment, implant 10 is sheathed at the top and bottom with a separate dielectric layer such as LCP or silicone, that is 80 $\mu$m (3 mils) thick.

A typical, and challenging, application for an electrode bearing implant, such as implant 10, is as a cochlear implant. One of the great challenges of creating a cochlear implant is creating a structure that is helical and may be straightened for purposes of insertion but will then resume its helical shape. A characteristic of laminated structures is that they tend to bend more easily along the plane that intersects the laminae, than along the plane that is parallel with the laminae.

Referring to FIG. 3, one approach to creating a cochlear implant is to create a laminated structure 50 that extends far enough in two dimensions to accommodate a cochlear spiral shape 52. The structure 50 is built with traces 14 in spiral shape within structure 50. Traces 14 terminate on the interior surface 56 of spiral shape 52, which is cut from structure 50, to form a helical implant 58. The electrode contact points 22 in this instance may be constructed on the side of and/or on top of helical implant 58 to make as close as contact as possible with the receptive neurons or nerve cells, located along the upper and inner side of the scala media. The helical implant 58 may then be heat formed, by placing it in a helical mold 60, either by itself or with a charge of silicone and or LCP. Helical mold 60 is made of a center conical part 62 and two halves 64 that meet about part 62.

In an alternative preferred embodiment implant 10 is originally made straight, as in FIG. 1, and then placed in the helical mold 60, curling in the plane that intersects the laminae. Mold 60 may be heated to form implant 10 into a spiral structure 66. This structure could then be straightened for insertion, but would have shape memory to revert to a spiral or helical shape after insertion.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A bio-implant having a length and a proximal and a distal end, said bio-implant comprising:
   (a) at least a first, second and third lamina of dielectric material joined together, thereby defining boundaries between said lamina and also defining a side surface that is intersected by said boundaries;
   (b) at least a first set of conductors interposed between said first and second lamina and a second set of conductors interposed between said second and third lamina, said first and second set of conductors extending lengthwise from said proximal end toward said distal end, each one of said set of conductors being terminated at said side surface to form a set of conductor terminations; and (c) a set of electrode contacts constructed on said side surface, each said electrode contact contacting one of said conductor terminations.

2. The bio-implant of claim 1 further being defined as helical in shape.

3. The bio-implant of claim 1 wherein said side surface includes inward recesses positioned transversely to said length of said bio-implant and wherein said electrode contact points take the form of conductive plating on said inward recesses.

4. The bio-implant of claim 3 wherein said contact points are recessed inwardly.

5. The bio-implant of claim 1 wherein said conductor terminations abut said side surface.

6. A method of constructing a bio-implant having a length and a proximal and a distal end, said method comprising:

(a) providing a first, second and third lamina of dielectric material, each said lamina defining a top surface, a bottom surface, a lamina side surface, a proximal end and a distal end, said bottom surface of said first layer and said top surface of said second layer being termed a pair of first surfaces and said bottom surface of said second layer and said top surface of said third layer being termed a pair of second surfaces;

(b) providing at least a first set of conductors positioned on said pair of first surfaces and a second set of conductors positioned on said pair of second surfaces, said first and second sets of conductors extending lengthwise from said proximal end toward said distal end, each one of said set of conductors being terminated adjacent to said side surface to form a set of conductor terminations;

(c) adhering said second lamina to said first lamina about said first set of conductors, and adhering said third lamina to said second lamina about said second set of conductors thereby defining a boundary and also defining a joined side surface that is intersected by said boundary; and (d) forming a set of electrode contact points constructed on said joined side surface, each said electrode contact point contacting a one of said conductor terminations.

7. The method of claim 6 wherein inward recesses are formed in said joined side surface, said inward recesses positioned transversely to said length of said bio-implant and conductive material is plated onto said inward recesses to form said contact points.

8. The method of claim 7 wherein said contact points are recessed inwardly.

* * * * *

UNITED STATES PATENT AND TRADEMARK OFFICE
CERTIFICATE OF CORRECTION

PATENT NO. : 6,678,564 B2
DATED : January 13, 2004
INVENTOR(S) : Ketterl et al.

It is certified that error appears in the above-identified patent and that said Letters Patent is hereby corrected as shown below:

<u>Title page,</u>
Item [56], References Cited, U.S. PATENT DOCUMENTS add:
-- 4,871,595   10/1989      Lusignea et al.       428/1
   4,975,312   12/1990      Lusignea et al.       428/209
   5,137,618   08/1992      Burnett et al.        205/125
   5,720,099   02/1998      Parker et al.         29/825 --
Insert -- FOREIGN PATENT DOCUMENTS,
WO 01/12115 A1       02/2001         WIPO --

Signed and Sealed this

Thirteenth Day of April, 2004

JON W. DUDAS
*Acting Director of the United States Patent and Trademark Office*